(12) United States Patent
Igaki

(10) Patent No.: US 8,636,790 B2
(45) Date of Patent: Jan. 28, 2014

(54) VASCULAR STENT

(75) Inventor: Keiji Igaki, Kyoto (JP)

(73) Assignee: Kabushikikaisha Kyoto Iryo Sekkei, Kyoto (JP)

( * ) Notice: Subject to any disclaimer, the term of this patent is extended or adjusted under 35 U.S.C. 154(b) by 21 days.

(21) Appl. No.: 13/001,259

(22) PCT Filed: Jun. 19, 2009

(86) PCT No.: PCT/JP2009/002804
§ 371 (c)(1),
(2), (4) Date: Mar. 28, 2011

(87) PCT Pub. No.: WO2009/157164
PCT Pub. Date: Dec. 30, 2009

(65) Prior Publication Data
US 2011/0184506 A1    Jul. 28, 2011

(30) Foreign Application Priority Data
Jun. 27, 2008   (JP) .............................. P2008-169358

(51) Int. Cl.
*A61F 2/82*   (2013.01)

(52) U.S. Cl.
USPC ........................................ 623/1.15; 623/1.16

(58) Field of Classification Search
USPC .............................................. 623/1.11–1.19
See application file for complete search history.

(56) References Cited

U.S. PATENT DOCUMENTS

| | | | | |
|---|---|---|---|---|
| 6,004,346 A | * | 12/1999 | Wolff et al. ................ | 623/23.71 |
| 6,056,775 A | * | 5/2000 | Borghi et al. ................ | 623/1.16 |
| 6,113,628 A | * | 9/2000 | Borghi .......................... | 623/1.16 |
| 6,500,204 B1 | | 12/2002 | Igaki | |
| 6,551,351 B2 | * | 4/2003 | Smith et al. ................ | 623/1.16 |
| 6,730,117 B1 | * | 5/2004 | Tseng et al. ................ | 623/1.16 |
| 6,818,076 B1 | * | 11/2004 | Farzin-Nia ................... | 148/421 |
| 7,335,226 B2 | * | 2/2008 | Igaki ............................ | 623/1.15 |
| 7,367,990 B2 | * | 5/2008 | Igaki ............................ | 623/1.44 |
| D622,387 S | * | 8/2010 | Igaki ............................ | D24/155 |

(Continued)

FOREIGN PATENT DOCUMENTS

EP   1 813 231 A1   8/2007
JP   11-057018       3/1999

(Continued)

OTHER PUBLICATIONS

International Search Report dated Jul. 8, 2009, for corresponding Patent Application PCT/JP2009/002804.

(Continued)

*Primary Examiner* — Suzette J Gherbi
(74) *Attorney, Agent, or Firm* — K&L Gates LLP

(57) ABSTRACT

A vascular stent to be implanted in a vessel of a living body to scaffold the vessel from inside is provided. The stent includes a tubular body formed by assembling a plurality of tubular-body forming elements constituting a part of a tubular body. The tubular-body forming elements are formed by bending a strand made of a biodegradable polymer such that legs as linear parts and bend parts alternate in sequence, to form a single flow channel from one end to the other end. The plurality of tubular-body forming elements constitute the tubular body by connecting and unifying two connecting members by melt welding, each of the connecting members being attached to adjacent portions of the plurality of tubular-body forming elements.

23 Claims, 8 Drawing Sheets

(56) References Cited

U.S. PATENT DOCUMENTS

| | | | |
|---|---|---|---|
| 7,896,899 B2* | 3/2011 | Patterson et al. | 606/200 |
| 8,070,793 B2* | 12/2011 | Igaki | 623/1.15 |
| 2001/0009982 A1* | 7/2001 | Ferrera et al. | 600/585 |
| 2001/0010015 A1* | 7/2001 | Hijlkema | 623/1.16 |
| 2001/0012960 A1* | 8/2001 | Acciai et al. | 623/1.15 |
| 2001/0021871 A1* | 9/2001 | Stinson | 623/1.15 |
| 2002/0156525 A1* | 10/2002 | Smith et al. | 623/1.22 |
| 2004/0162606 A1* | 8/2004 | Thompson | 623/1.22 |
| 2004/0220606 A1 | 11/2004 | Goshgarian | |
| 2007/0026132 A1* | 2/2007 | Williams et al. | 427/2.25 |
| 2007/0282428 A1 | 12/2007 | Igaki | |
| 2008/0103584 A1* | 5/2008 | Su et al. | 623/1.16 |
| 2008/0319529 A1* | 12/2008 | Krivoruchko et al. | 623/1.16 |
| 2009/0125099 A1* | 5/2009 | Weber et al. | 623/1.34 |
| 2009/0192592 A1* | 7/2009 | Asgari | 623/1.39 |
| 2009/0276029 A1* | 11/2009 | Caro et al. | 623/1.11 |
| 2010/0030319 A1* | 2/2010 | Weber | 623/1.11 |
| 2010/0198333 A1* | 8/2010 | Macatangay et al. | 623/1.15 |
| 2010/0274350 A1* | 10/2010 | Richter | 623/1.22 |
| 2011/0015721 A1 | 1/2011 | Tseng et al. | |
| 2011/0071616 A1* | 3/2011 | Clarke et al. | 623/1.16 |
| 2011/0184506 A1* | 7/2011 | Igaki | 623/1.16 |
| 2011/0319977 A1* | 12/2011 | Pandelidis et al. | 623/1.15 |
| 2012/0109283 A1* | 5/2012 | Burkart et al. | 623/1.16 |
| 2012/0197384 A1* | 8/2012 | Lee et al. | 623/1.15 |

FOREIGN PATENT DOCUMENTS

| | | |
|---|---|---|
| JP | 2004-033579 | 2/2004 |
| JP | 2004-329924 | 11/2004 |
| WO | 92/15342 | 9/1992 |
| WO | 99/44535 | 9/1999 |
| WO | 99/44535 A1 | 9/1999 |
| WO | 00/13737 | 3/2000 |
| WO | 2006/051912 | 5/2006 |
| WO | 2008-015873 A1 | 2/2008 |

OTHER PUBLICATIONS

European search report for corresponding EP09769874.0-1651 issued on Feb. 13, 2013.

* cited by examiner

VASCULAR STENT

CROSS REFERENCE TO RELATED APPLICATIONS

The present application is a National Stage of International Application No. PCT/JP2009/002804 filed on Jun. 19, 2009 and which claims priority to Japanese Patent Application No. JP2008-169358 filed on Jun. 27, 2008, the entire contents of which are being incorporated herein by reference.

BACKGROUND

The present disclosure relates to a cylindrically-shaped element for a vascular stent deployed in a vessel in a living body, such as a blood vessel, trachea or biliary duct, to scaffold the inner lumen of the vessel from inside, ensuring a flow channel in the vessel.

Heretofore, when stenosis occurs in a vessel of a living body such as a blood vessel including an artery, percutaneous transluminal angioplasty (PTA) is performed in which the stenosed portion in the vessel is expanded to improve the blood flow by inserting a balloon provided in the vicinity of the end of a balloon catheter and then inflating the balloon which is contracted initially.

Meanwhile, it is known that despite PTA applied initially, stenosis tends to recur at a high probability in the once stenosed site.

The current practice for prevention of such restenosis is to implant a cylindrical stent in the site treated with PTA. The stent is intended to scaffold a blood vessel from inside for the purpose of prevention of restenosis therein by being inserted into the blood vessel with its contracted state and subsequently expanded to be implanted therein.

As such a sort of stent, a stent comprised of a cylindrical metal member with slits to permit its expansion or contraction in diameter has been currently known.

Meanwhile, use of metal stents may lead to foreign-body reaction due to its long term presence in a living body, it is therefore not appropriate to leave them therein semi-permanently. Moreover, removal of metal stents after its deployment in a living body if needed, requires surgical procedures that impose severe burden on the patient.

To solve such inherent problems with metal stents, the present inventor has proposed a stent made of a biodegradable polymer in International Patent Publication Nos. WO92/15342 (Patent Document 1) and WO00/13737 (Patent Document 2).

A stent made of a biodegradable polymer has also been proposed in JP Laid-Open Patent Publication Nos. H-11-57018 (Patent Document 3) and 2004-33579 (Patent Document 4).

Furthermore, a vascular stent wherein several strands bent in zigzag are connected together to form a tubular body is disclosed in WO99/44535 (Patent Document 5).

SUMMARY

The vascular stent formed of the cylindrically-shaped elements according to the embodiment is implanted in a vessel of a living body, such as blood vessel including coronary artery, trachea or biliary duct, to be used as a member for scaffolding the vessel from the inside. The vascular stent formed of a biodegradable polymer material is implanted in a vessel in a living body and then disappears in the living body after a period of time It is desirable that a stent implanted in a vessel of a living body have such flexibility that it deforms easily in accordance with a sinuous or meandering vessel in order to achieve smooth insertion into a vessel.

In addition, a stent should have sufficient strength to surely scaffold an inner wall of a vessel, such as a blood vessel, keeping the vessel in a diameter-expanded state, such that humor, such as blood flow, flows through the vessel, when the stent is implanted in the vessel.

Furthermore, it is desirable that a vascular stent expands and scaffolds the inner wall of a vessel with radially even force to avoid injury therein.

Therefore it is desired to provide a vascular stent having an advantage of using a biodegradable polymer and excellent biocompatibility.

It is also desired to provide a vascular stent using the biodegradable polymer which has excellent flexibility, sufficient radial force to support an inner wall of a vessel, such as a stenosed blood vessel, and ability to expand and scaffold the inner wall of the vessel with uniform force.

Moreover, it is desired to provide a vascular stent which can be manufactured efficiently to allow excellent productivity.

A vascular stent according to tan embodiment is formed by a tubular body combined with a plurality of tubular-body forming elements to provide a single flow channel from one end to the other therein, the tubular-body forming elements being formed by bending a strand made of biodegradable polymer such that a linear part and a bend part alternate in sequence, wherein said tubular-body forming elements are combined together to form the single tubular body by melt-welding at least two connecting members made of biodegradable polymer, the connecting members each being attached to the adjacent portions of the adjacent tubular-body forming elements.

In the tubular-body forming elements used herein, the bend parts are arranged in multistage along the axial direction of the tubular body formed of the tubular-body forming elements by, for example, making some of the linear parts longer than the others.

In addition, the tubular-body forming elements, when assembled as the tubular body, are wound in a cylindrical shape to form the outer surface of the tubular body.

In an embodiment, the connecting member connecting each of the tubular-body forming elements are formed of the substantially same type of biodegradable polymer as that of used in the strand and have a melting point (Tm) lower than that of the biodegradable polymer forming the strand.

In an embodiment, the strand and the connecting member be formed of the substantially same type of polylactic acid.

Furthermore, in an embodiment, a plurality of tubular-body forming elements are combined to form the tubular body without an overlapping portion.

In addition, in an embodiment, the connecting members connecting a plurality of tubular-body forming elements are spirally arranged on the outer surface of the tubular body Furthermore, in an embodiment, the strand forming the tubular-body forming element is a non-interrupted continuous monofilament Since the vascular stent according to the embodiment is formed by melt-welding and unifying two connecting members made of biodegradable polymer, the connecting members being attached to adjacent portions of a plurality of adjacent tubular-body forming elements formed by bending a strand made of biodegradable polymer such that a linear part and a bend part alternate in sequence, a plurality of tubular-body forming elements constituting the tubular body can be combined and held tightly, maintaining the configuration of the tubular body with a single flow channel from one end to the other therein. The vascular stent according to the embodiment, therefore, can maintain its original cylindrical shape after its deployment in a vessel of a living body, ensuring a flow channel to be formed in the vessel.

Moreover, since a plurality of tubular-body forming elements are unified by melt-welding the connecting members attached to them, thermal effect on these tubular-body forming elements is small. Consequently, the manufacture of the vascular stent which can ensure prevention of variation incrystallinity and molecular weight of the tubular-body forming elements, unchanged preset physical properties, even radial strength to scaffold the inner wall of a vessel when implanted in the vessel, and desired scaffolding strength.

By forming the connecting member with a biodegradable polymer having a melting point (Tm) lower than that of the biodegradable polymer forming the strand, the tubular-forming elements can be unified without thermal effect on them.

Furthermore, since the vascular stent according to the embodiment is entirely made of biodegradable polymer, safety for implantation in a living body is ensured. In particular, since the vascular stent of the embodiment is formed without use of adhesives, no impurity other than biodegradable polymers is mixed in the stent, ensuring sufficient safety for implantation in a living body.

Furthermore, since the tubular-body forming elements assembled as the tubular body are wound in a cylindrical shape to form outer surface of the tubular body, deformation of the tubular body as a whole is facilitated, ensuring flexibility to deform easily in accordance with curvatures of vessels. In particular, since the tubular-body forming elements are unified with the spirally-arranged connecting members on the outer surface of the tubular body, the deformation along the axial direction can be more surely facilitated ensuring flexibility to deform easily in accordance with a sinuous vessel.

Furthermore, several pairs of connecting members to be connected to unify the plurality of tubular-body forming elements are connected by melt-welding at one step rather than repeated steps in which each pair is joined, to realize efficient manufacturing and thus improved productivity.

In addition, by forming the strand with a monofilament, the uniform physical and chemical properties of the tubular-body forming elements made by such strand, subsequently, the uniform physical and chemical properties of the vascular stent using such tubular-body forming elements as well, can be achieved.

Additional features and advantages are described herein, and will be apparent from, the following Detailed Description and the figures.

DETAILED DESCRIPTION

Figure 1:
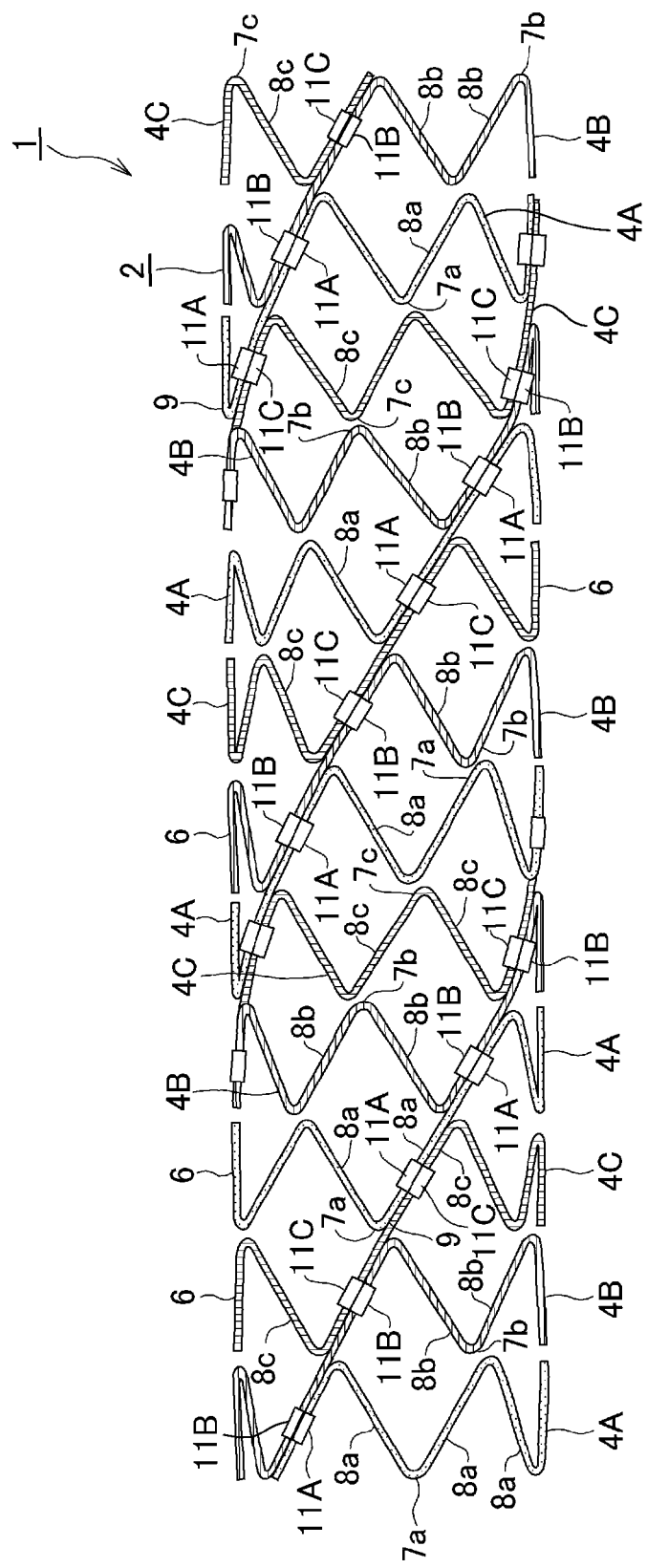
FIG. 1 is a side view showing one side of a vascular stent according to an embodiment.

Referring to the drawings, embodiments of the vascular stent acc are explained in detail.

Figure 2:
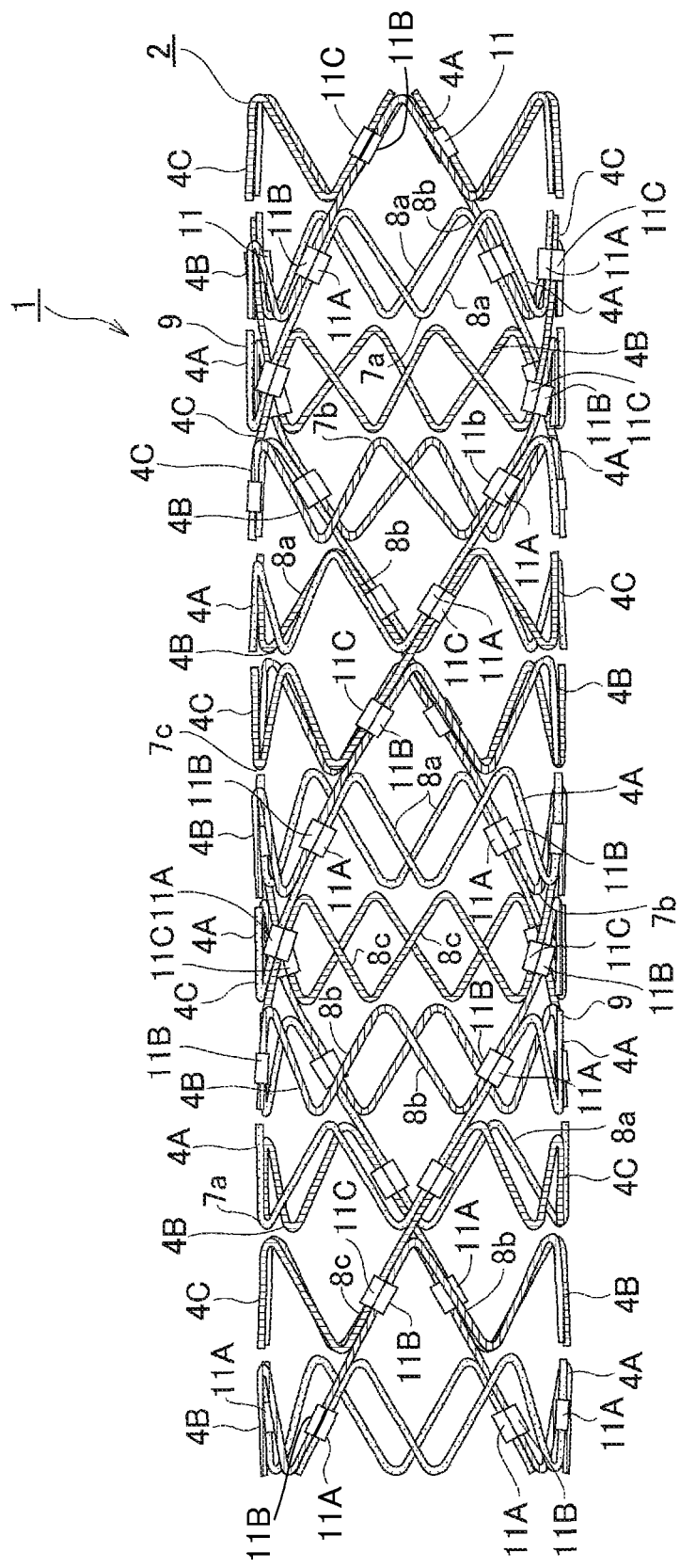
FIG. 2 is a perspective view showing a vascular stent according to an embodiment.

The vascular stent 1 shown here is used to implant in a blood vessel such as a peripheral vessel in a living body, and formed by a cylindrical tubular body 2 as shown in FIGS. 1 and 2.

FIG. 1 is a side view of only the half outer surface of the cylindrically shaped tubular body 2. FIG. 2 is a side view showing the entire tubular body 2.

Dimensions of the vascular stent 1 applied the embodiment are appropriately selected in accordance with a vessel of a living body in which the vascular stent 1 is to be implanted. For example, the vascular stent 1 intended for a blood vessel is configured to have an outer diameter R1 of 5 to 8 mm and a length L1 of 25 to 80 mm. These dimensions are appropriately determined in accordance with the size of a vessel of a living body in which the vascular stent 1 is to be implanted, and obtained after the vascular stent 1 has been implanted in the vessel of the living body.

This vascular stent 1 comprises the tubular body 2 formed by combining a plurality of tubular-body forming elements 4, the tubular-body forming elements being formed by bending a non-interrupted continuous strand 3 made of biodegradable polymer such that a linear part and a bend part alternate in sequence. As shown in FIGS. 1 and 2, this tubular body 2 is cylindrically-shaped in which a single flow channel is formed from one end to the other end.

In this embodiment, the tubular body 2 is constituted by combining three tubular-body forming elements 4A, 4B and 4C. It should be noted that, in the following description, tubular-body forming elements 4 represents tubular-body forming elements 4A, 4B and 4C collectively.

This strand 3 constituting the tubular-body forming element 4 is formed of the biodegradable polymer which does not cause adverse reaction therein when implanted in a living body, such as a human body. The biodegradable polymer to be used may be polylactic acid (PLA), polyglycolic acid (PGA), polyglactin (copolymer of polyglycolic acid and polylactic acid), polydioxanone, polyglyconate (copolymer of trimethylene carbonate and glycolid), or copolymer of polyglycolic acid or polylactic acid and 8-caprolactone. In addition, the biodegradable polymers obtained by compounding two or more of these materials can be used.

The use of biodegradable polymer, poly-L-lactic acid (PLLA) is desirable herein based on its safety in a living body.

The strand 3 is formed of a continuous monofilament composed of biodegradable polymer and/or a multifilament composed of multiple monofilaments unified together. These monofilaments and/or multifilaments may be formed by, for example, melt-spinning biodegradable polymer with a melt-spinning apparatus. Whether to use these monofilaments and/or multifilaments depends on the strength and biodegradable properties of the strand 3.

Figure 4:
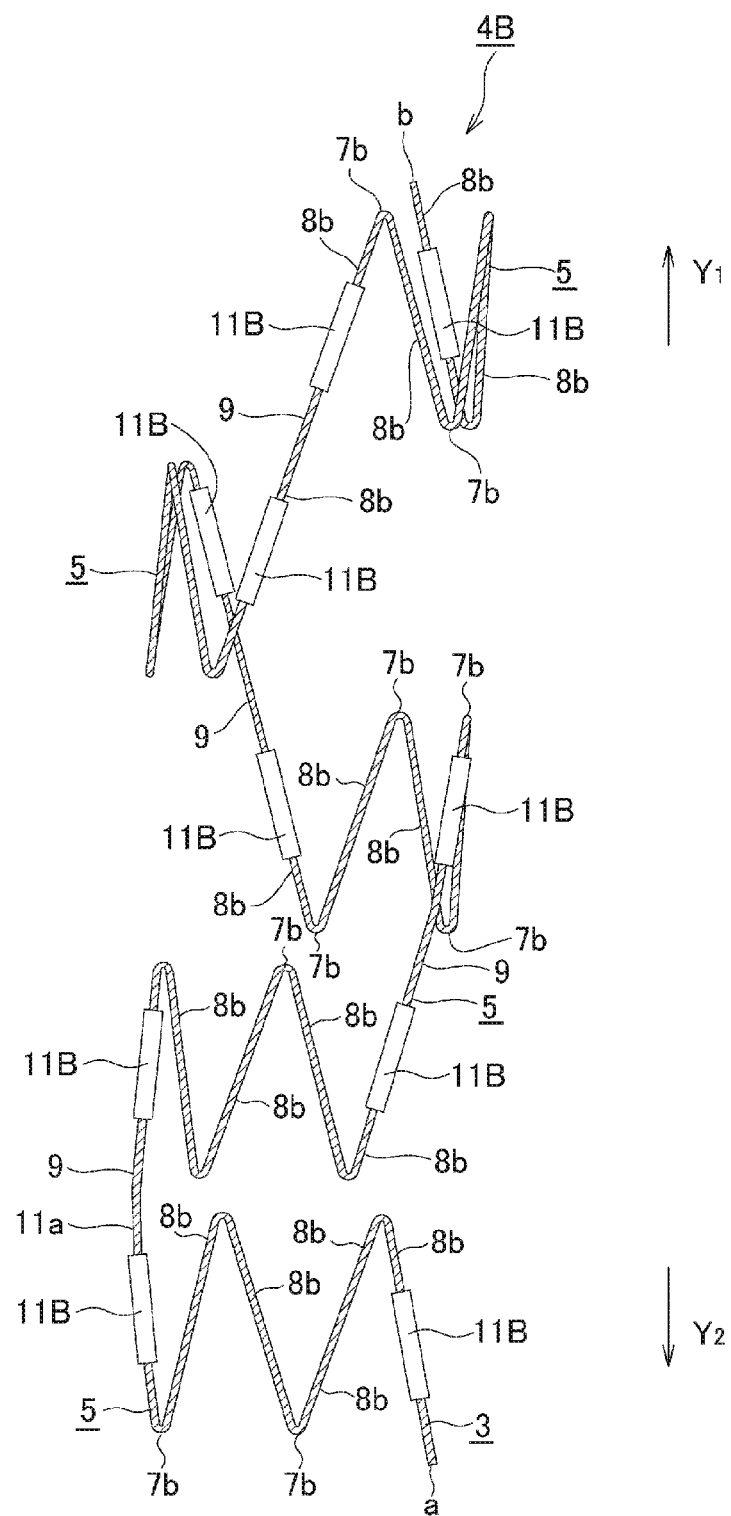
FIG. 4 is a side view showing a second tubular-body forming element constituting a vascular stent according to an embodiment.
Figure 5:
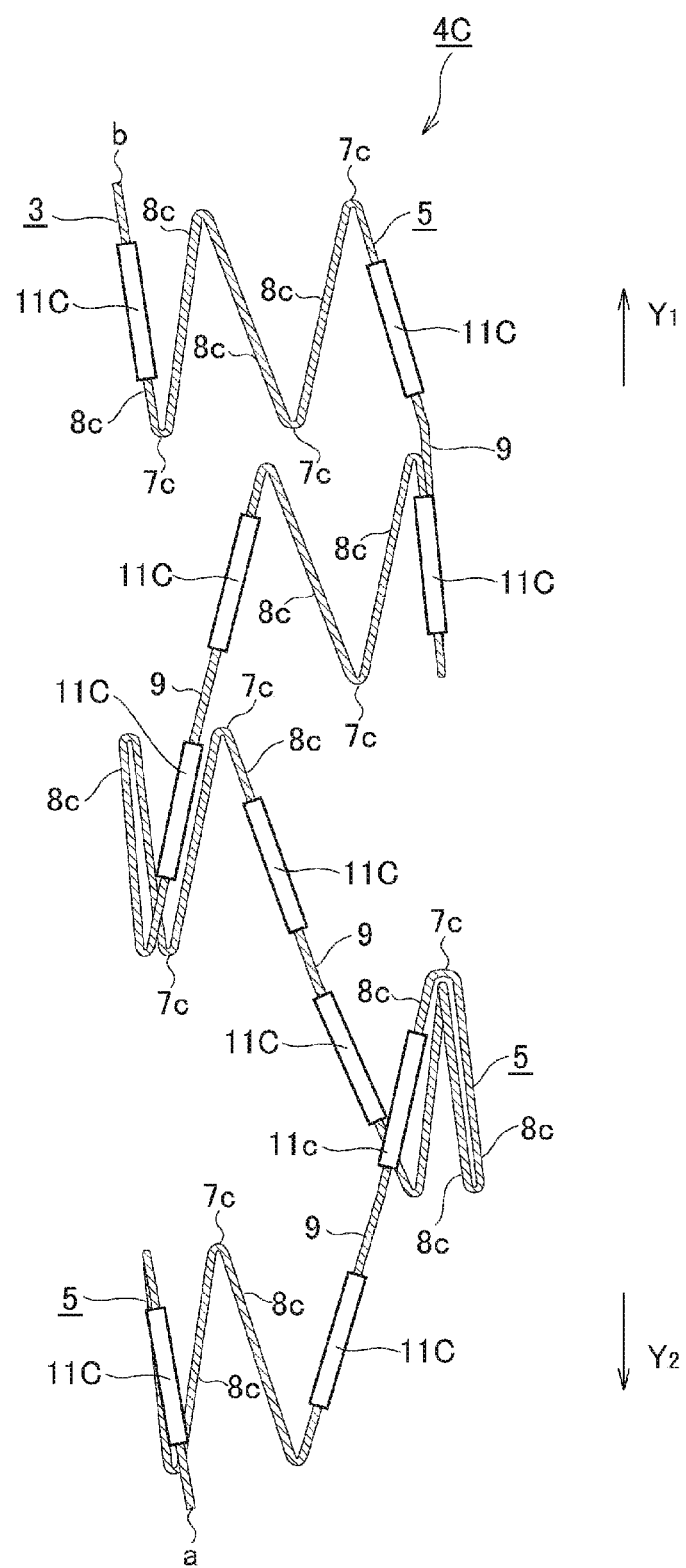
FIG. 5 is a side view showing a third tubular-body forming element constituting a vascular stent according to an embodiment.

In this embodiment, as shown in FIGS. 1 and 2, the tubular body 2 is constituted by combining three tubular-body forming elements 4A, 4B and 4C. Each of these first, second and third tubular-body forming elements 4A, 4B and 4C is formed by bending a continuous single strand 3 as shown in FIGS. 3, 4 and 5.

The first, second and third tubular-body forming elements 4A, 4B and 4C are now described in further detail.

Figure 3:
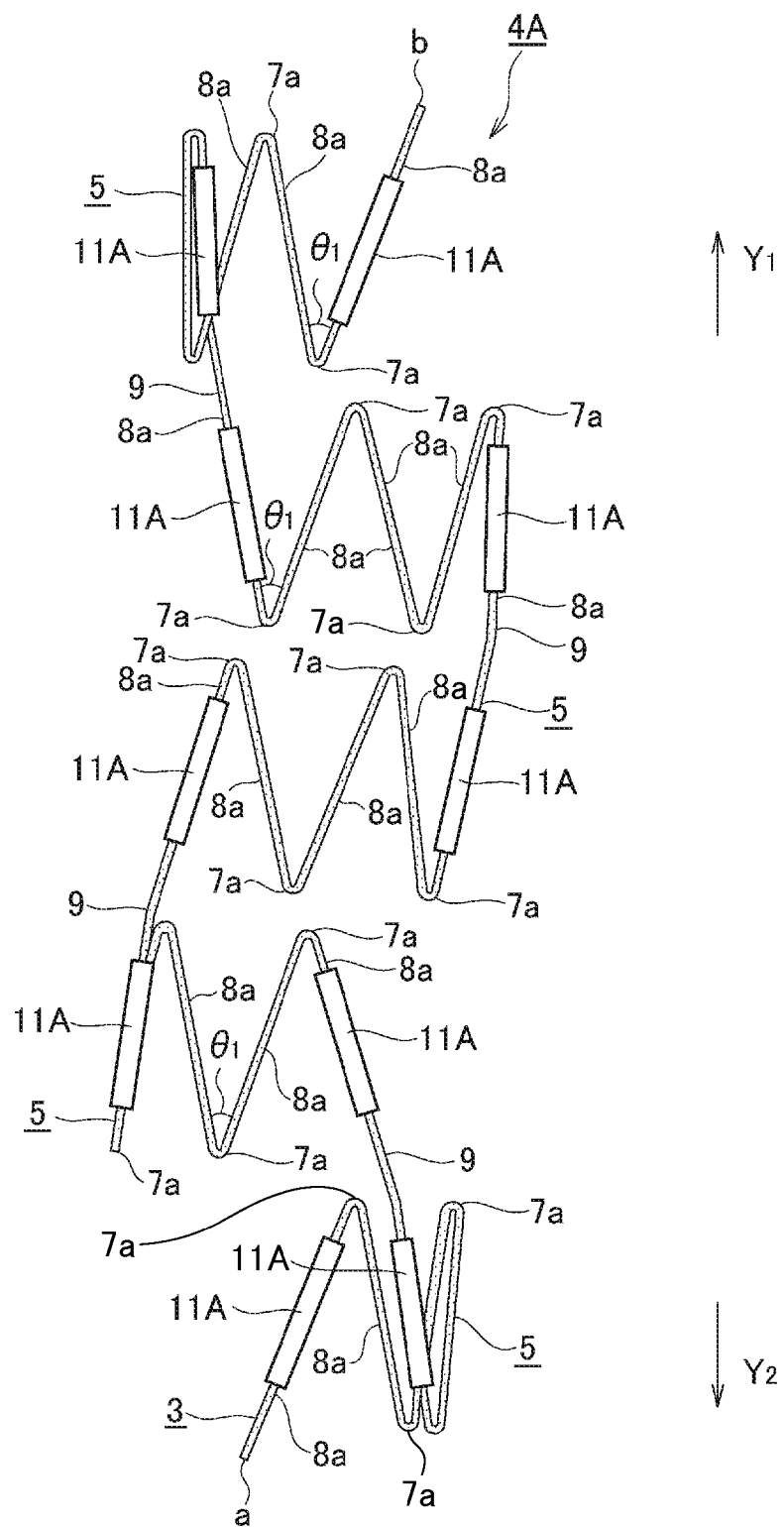
FIG. 3 is a side view showing a first tubular-body forming element constituting a vascular stent according to an embodiment.

Firstly, as shown in FIG. 3, the first tubular-body forming element 4A is formed by bending a single strand 3 in a zigzag design such that a linear part and a bend part alternate in sequence to produce two peaks and two valleys per one stage. Specifically, this tubular-body forming element 4A is formed by bending the single strand 3 such that starting from its one end, "a", at the lower left on FIG. 3, the first bend part 7 is angled in the direction of the arrow Y1 in FIG. 3 and then the next bend part 7 is angled in the direction of the arrow Y2 in FIG. 3.

The first tubular-body forming element 4A formed herein is combined with the second and third tubular-body forming elements 4B and 4C to constitute the cylindrical tubular body 2, and constitutes one-third of this tubular body 2.

Moreover, the strand 3 bent to form the single tubular-body forming element 4A is bent such that the pairs of legs 8a and 8a on both sides of the bend part 7a are same in length. The pair of legs 8a and 8a formed by being bent in V-shape or U-shape at the bend part 7a are displaced increasing or decreasing the angle θ1 formed by these legs 8a and 8a with the bend part 7a as the displacing point.

In the first tubular-body forming element 4A formed by bending the strand 3, the portion in which the strand 3 is bent in a zigzag design such that two pairs of peaks and valleys alternate in sequence, constitutes a tubular-body forming section 5. This tubular-body forming section 5, when combined with other tubular-body forming sections of other tubular-body forming elements 4, constitutes a single tubular section 6. Since the single tubular-body forming section 5 is constituted with the portion in which two pairs of peaks and valleys alternate in sequence, when the first bend part 7 starting from the "a" end is angled in the direction of the arrow Y1 in FIG. 3, then in the opposite end of the bending comes the bend part 7 angled in the direction of the arrow Y2 in FIG. 3. Consequently, the strand 3 extends in the direction of the arrow Y1 in FIG. 3 upwardly from the "b" end of the bending.

The strand 3 extending in the direction of the arrow Y1 in FIG. 3 from the tubular-body forming section 5 of the lowest first stage in FIG. 3 forms the tubular-body forming section 5 of the second stage by being bent in a zigzag design such that the new bending starts from joint section 9 extending toward the tubular-body forming section 5 of the second stage and two pairs of the peaks and valleys alternate in sequence. Here, the tubular-body forming section 5 of the second stage is bent such that the tip of the bend part 7 angled in the direction of the arrow Y2 in FIG. 3 is not overlapped with the tip of the bend part 7 of the tubular-body forming section 5 of the first stage angled in the direction of the arrow Y1 in FIG. 3.

That is, the tubular-body forming section 5 of the second stage is bent such that the tip of the bend part 7a of the second stage and the tip of the bend part 7a of the first stage make a gap between them or contact each other without overlapping.

Starting point of the bending for the tubular-body forming section 5 of the second stage is displaced from those for the tubular-body forming section 5 of the first stage by approximately 120 degree on the circumference of the tubular body 2 to be formed.

Moreover, the strand 3 extending in the direction of the arrow Y1 in FIG. 3 from the tubular-body forming section 5 of the second stage is then bent in zigzag design to form the tubular-body forming section 5 of the third stage by bending such that the bending starts from the joint section 9 extending toward the tubular-body forming section 5 of the third stage and two pairs of the peaks and valleys alternate in sequence. Here, the tubular-body forming section 5 of the third stage is bent such that the tip of the bend part 7 angled in the direction of the arrow Y2 in FIG. 3 is not overlapped with the tip of the bend part 7 of the tubular-body forming section 5 of the second stage angled in the direction of the arrow Y1 in FIG. 3.

Starting point of the bending for the tubular-body forming section 5 of the third stage is displaced from those for the tubular-body forming section 5 of the second stage by approximately 120 degree on the circumference of the tubular body 2 to be formed.

Moreover, the strand 3 extending in the direction of the arrow Y1 in FIG. 3 from the tubular-body forming section 5 of the third stage in FIG. 3 forms the tubular-body forming section 5 of the fourth stage by being bent in a zigzag design such that the bending starts from the joint section 9 extending toward the tubular-body forming section 5 of the fourth stage and two pairs of the peaks and valleys alternate in sequence. Here, the tubular-body forming section 5 of the fourth stage is bent such that the tip of the bend part 7 angled in the direction of the arrow Y2 in FIG. 3 is not overlapped with the tip of the bend part 7 of the tubular-body forming section 5 of the third stage angled in the direction of the arrow Y1 in FIG. 3.

The starting point of the bending for the tubular-body forming section 5 of the fourth stage is displaced from those for the tubular-body forming section 5 of the third stage by approximately 120 degree on the circumference of the tubular body 2 to be formed.

Moreover, the strand 3 extending in the direction of the arrow Y1 in FIG. 3 from the tubular-body forming section 5 of the fourth stage in FIG. 3 forms the tubular-body forming section 5 of the fifth stage by being bent in a zigzag design such that the bending starts from the joint section 9 extending toward the tubular-body forming section 5 of the fifth stage and two pairs of the peaks and valleys alternate in sequence. Here, the tubular-body forming section 5 of the fifth stage is bent such that the tip of the bend part 7 angled in the direction of the arrow Y2 in FIG. 3 is not overlapped with the tip of the bend part 7 of the tubular-body forming section 5 of the fourth stage angled in the direction of the arrow Y1 in FIG. 3.

The starting point of the bending for the tubular-body forming section 5 of the fifth stage is displaced from those for the tubular-body forming section 5 of the fourth stage by approximately 120 degree on the circumference of the tubular body 2 to be formed.

If the sixth and further stages are provided in the tubular-body forming section 5, they are formed by bending the strand 3 in the above sequence.

Similarly to the first tubular-body forming element 4A, the second tubular-body forming element 4B is also formed by bending a single strand 3 as shown in FIG. 4.

The second tubular-body forming element 4B also has the same configuration as the first tubular-body forming element 4A, being formed by bending a single strand 3 in a zigzag design such that a linear part, leg 8b, and a bend part 7b alternate in sequence to produce two peaks and two valleys per one stage. By labeling the bend parts formed in the second tubular-body forming element 4B as 7b and the legs therein as 8b, the description of the configuration of the first tubular-body forming element 4A can be applied to the second tubular-body forming element 4B in order to omit further explanation for it.

This second tubular-body forming element 4B is also combined with the first and third tubular-body forming elements 4A and 4C to constitute the cylindrical tubular body 2, constituting one-third of this tubular body 2.

That is, as is the case of the first tubular-body forming element 4A, the second tubular-body forming element 4B includes peaks and valleys constituted by a pair of left and right legs 8b and 8b on both sides of a bend part 7b.

Furthermore, similarly as the first and second tubular-body forming elements 4A and 4B, the third tubular-body forming element 4C is also formed by bending a single strand 3 as shown in FIG. 5.

The third tubular-body forming element 4C also has the same configuration as the first and second tubular-body forming elements 4A and 4C, being formed by bending a single strand 3 in a zigzag design such that a leg 8c as a linear part and a bend part 7c alternate in sequence to produce two peaks and two valleys per one stage. By labeling the bend parts formed in the second tubular-body forming element 4C as 7c and the legs therein as 8c, the description of the configuration of the first tubular-body forming element 4A can be applied to the third tubular-body forming element 4C to omit further explanation for it.

This third tubular-body forming element 4C is also combined with the first and second tubular-body forming elements 4A and 4B to constitute the cylindrical tubular body 2, and constitutes one-third of this tubular body 2.

That is, as is the case of the first and second tubular-body forming elements 4A and 4B, the third tubular-body forming element 4C includes peaks and valleys constituted by a pair of left and right legs 8c and 8c on both sides of a bend part 7c.

It should be noted that the first, second and third tubular-body forming elements 4A, 4B and 4C are combined to constitute the single tubular body 2, so the same number of tubular-body forming sections 5 are formed in each tubular-body forming element 4.

In addition, the first, second and third tubular-body forming elements 4A, 4B and 4C are provided with an appropriate number of tubular-body forming sections 5 depending on the length of the tubular body 2 to be constituted and the height of the peaks and valleys bent in a zigzag design. That is, the FIGS. 3, 4 and 5 show merely one example of the tubular-body forming elements 4, so the height and depth of the peaks and valleys bent in a zigzag design and the number of tubular-body forming sections 5 are selected according to the size of the vascular stent 1 to be formed.

The single set of the first, second and third tubular-body forming elements 4A, 4B and 4C configured as above are combined with each other to form the single tubular body 2 as shown in FIGS. 1 and 2.

Specifically, the first, second and third tubular-body forming elements 4A, 4B and 4C are combined together to form the single tubular body 2 by bending the tubular-body forming sections 5 in a zigzag design as shown in FIG. 1. The tubular-body forming sections 5 are combined in a stage-by-stage fashion to form a single stage of tubular sections 6 at a time.

Meanwhile, in the first, second and third tubular-body forming elements 4A, 4B and 4C, the tubular-body forming sections 5 positioned vertically are linked in multistage via the joint sections 9 linking legs 8a, 8b and 8c of these tubular-body forming sections 5. The tubular body 2, therefore, has the configuration in which the tubular sections 6 formed by combining the tubular-body forming sections 5 are linked in multistage via the joint sections 9.

The first, second and third tubular-body forming elements 4A, 4B and 4C are unified to form the single tubular body 2 by combining them together and connecting their adjacent legs 8a, 8b and 8c. That is, the first, second and third tubular-body forming elements 4A, 4B and 4C are unified to form the tubular body 2 by connecting the leg 8a of the first tubular-body forming element 4A and the adjacent leg 8b of the adjacent second tubular-body forming element 4B, connecting the leg 8a of the first tubular-body forming element 4A and the adjacent leg 8c of the adjacent third tubular-body forming element 4C, and connecting the leg 8b of the second tubular-body forming element 4B and the adjacent leg 8c of the adjacent tubular-body forming element 4C.

The connections for the adjacent pairs of legs 8a and 8b, the adjacent pairs of legs 8a and 8c, and the adjacent pairs of legs 8b and 8c of these first, second and third tubular-body forming elements 4A, 4B and 4C are conducted by melt-welding the adjacent pairs of the connecting members 11A and 11B, the adjacent pairs of the connecting members 11A and 11C, and the adjacent pairs of the connecting members 11B and 11C, as shown in FIGS. 1 and 2.

Each of the connecting members 11A, 11B and 11C is formed of the substantially same type of biodegradable polymer as the strand 3 constituting each of the tubular-body forming elements 4A, 4B and 4C. Specifically, both are formed by using poly-L-lactic acid (PLLA).

Each of the connecting members 11A, 11B and 11C is formed as a cylinder having a sufficient diameter to accommodate the legs 8a, 8b and 8c respectively, and the strand 3 to be bent is inserted therethrough in advance.

The connection for the adjacent connecting members 11A, 11B and 11C is performed by applying heat to the assembly constituted with the first, second and third tubular-body forming elements 4A, 4B and 4C to form the single tubular body 2.

Figure 6:
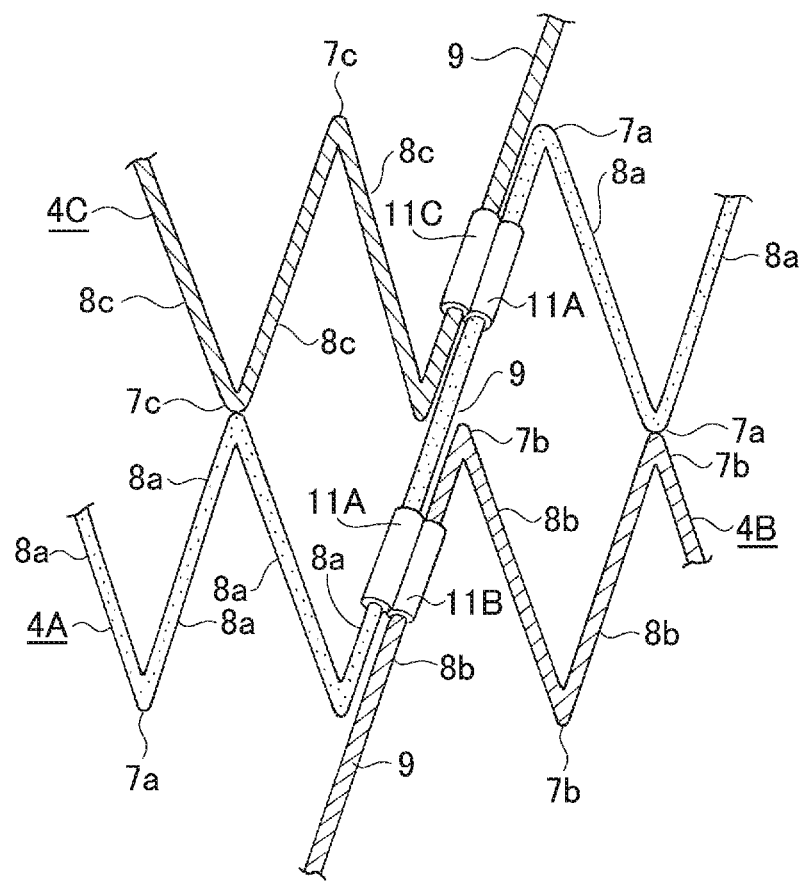
FIG. 6 is a side view showing tubular-body forming elements wherein connecting members are attached to their adjacent legs.
Figure 7:
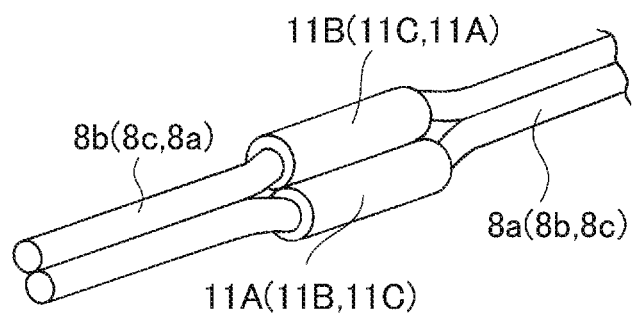
FIG. 7 is a perspective view showing tubular-body forming elements wherein connecting members attached to their adjacent legs are contacted each other.

Meanwhile, when the first, second and third tubular-body forming elements 4A, 4B and 4C are assembled to form the single tubular body 2, the portions where they contact each other are subject to contacting pressure. Since each of the connecting members 11A, 11B and 11C is on the outer surface of each of the legs 8a, 8b and 8c as shown in FIG. 6, the portions where the connecting members 11A, 11B and 11C are attached to the legs 8a, 8b and 8c bulge out from the other portions and larger in width than the other portions. When the first, second and third tubular-body forming elements 4A, 4B and 4C are assembled to form the single tubular body 2, the adjacent connecting members 11A, 11B and 11C, therefore, contact each other with pressure. When the first, second and third tubular-body forming elements 4A, 4B and 4C are assembled to form the single tubular body 2 and pressured from the outer side of the assembly to keep the assembled state, as shown in FIG. 7, the adjacent connecting members 11A, 11B and 11C get contacted each other deforming the attached legs 8a, 8b and 8c, thus producing larger contacting pressure on their contacted portions than on the other portions.

Generally, when pressure is applied to the materials, the melting points (Tm) of thermoplastic polymer materials, such as polylactic acid, become lower than their normal melting point. Consequently, when the first, second and third tubular-body forming elements 4A, 4B and 4C are assembled to form the single tubular body 2, the melting point (Tm) of the connecting members 11A, 11B and 11C contacting each other with larger pressure than that at the other portions becomes lower. That is, by forming the tubular-body forming elements 4A, 4B and 4C with the substantially same type of polymer materials as the connecting members 11A, 11B and 11C, lower melting point (Tm) of the connecting members 11A, 11B and 11C than the melting point (Tm) of the legs 8a, 8b, and 8c is obtained.

Figure 8:
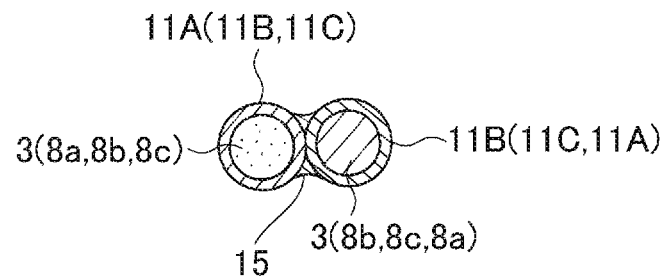
FIG. 8 is a cross-sectional view showing tubular-body forming elements wherein a pair of adjacent connecting members are joined by melt-welding.

By conducting a thermal process on the first, second and third tubular-body forming elements 4A, 4B and 4C combined and held such that the adjacent connecting members 11A, 11B and 11C are pressured more strongly than the other portions, thermal effect, such as thermal deformation of the strand 3 constituting these tubular-body forming elements 4A, 4B and 4C, can be avoided and only the adjacent several pairs of connecting members 11A, 11B and 11C is melt-welded to connect. That is, the tubular-body forming elements 4A, 4B and 4C are connected and unified via a melt-welded connecting portion 15 constituted with the contacting portions of the connecting members 11A, 11B and 11C, as shown in FIG. 8. Thus, thermal effect to the strand 3 constituting the tubular-body forming elements 4A, 4B and 4C and variations in its crystallinity and molecular weight is prevented not to change the physical and chemical properties of the strand 3.

Furthermore, in accordance with the vascular stent of the embodiment, by forming the connecting members 11A, 11B and 11C with the biodegradable polymer having the melting point (Tm) lower than that of the biodegradable polymer constituting the strand 3, thermal effect on the strand 3 during the melt-welding of the adjacent connecting members 11A, 11B and 11C is suppressed more surely. That is, by forming the connecting members 11A, 11B and 11C with the biodegradable polymer having the melting point (Tm) lower than that of the strand 3, when the first, second and third tubular-body forming elements 4A, 4B and 4C are assembled to form the tubular body 2, these connecting members 11A, 11B and 11C is melt without being effected by their contacting state at the temperature lower than the temperature at which the strand 3 would be melt. Consequently, when joining the connecting members 11A, 11B and 11C by melt-welding, thermal effect on the strand 3 that might alter the crystallinity and molecular weight of the biodegradable polymer constituting this strand 3 is avoided, thus keeping its preset physical and chemical properties unchanged.

A melting point (Tm) of biodegradable polymer could be changed by controlling crystallization conditions, such as crystallization temperature. Thus, the different melting points (Tm) are possible between the tubular-body forming elements 4A, 4B and 4C and the connecting members 11A, 11B and 11C, even if they are made of the substantially same type of biodegradable polymer.

A difference by ten degrees in temperature is desirable to melt-weld each of the connecting members 11A, 11B and 11C without generating thermal effect on the biodegradable polymer constituting the strand 3. That is, it is desirable to form the connecting members 11A, 11B and 11C with biodegradable polymer having a lower melting point than the biodegradable polymer constituting the strand 3 by ten degrees or more.

For the connection of the connecting members 11A, 11B and 11C, melting the entirety of the connecting members 11A, 11B and 11C is not always needed. It is sufficient to connect these connecting members 11A, 11B and 11C such that the legs 8a, 8b and 8c only avoid their detachment from the other legs by being connected with the connecting members 11A, 11B and 11C. Thus, the connecting members 11A, 11B and 11C may be partly melt-welded to connect.

When the connecting members 11A, 11B and 11C are melt-welded to connect, the whole of them could be melted and unified to become a spherical shape.

Figure 9:
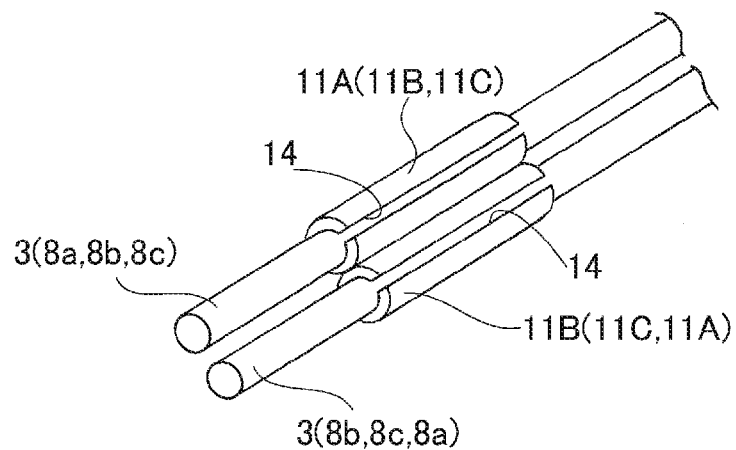
FIG. 9 is a perspective view showing another example of the connecting members.
Figure 10:
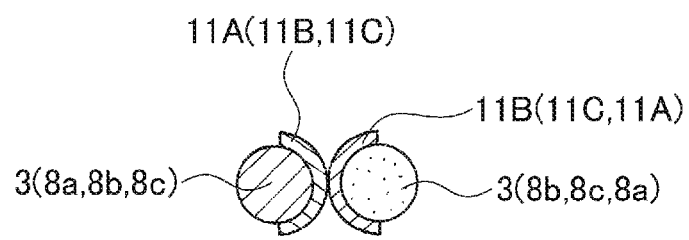
FIG. 10 is a cross-sectional view showing yet another example of the connecting members.

Although each of the connecting members 11A, 11B and 11C in the embodiment described above is formed into a cylindrical shape, these connecting members 11A, 11B and 11C can be of any shape that can be engaged with the outer surfaces of the legs 8a, 8b and 8c of the first, second and third tubular-body forming elements 4A, 4B and 4C. For example, as shown in FIG. 9, connecting members 11A, 11B and 11C with C-shaped cross section and having longitudinal gaps 14 along their axial direction may be used. These connecting members 11A, 11B and 11C having the longitudinal gaps 14 can be attached to the legs 8a, 8b and 8c after the strand 3 has been bent to form the tubular-body forming elements 4A, 4B and 4C Furthermore, as shown in FIG. 10, connecting members 11A, 11B and 11C with arc-shaped cross section and having a radius smaller than that of the legs 8a, 8b and 8c to which the connecting members 11A, 11B and 11C are attached may be used. The thus-shaped connecting members 11A, 11B and 11C can be attached to the legs 8a, 8b and 8c by being deformed elastically to clip the outer surface of the legs 8a, 8b and 8c.

That is, the connecting members 11A, 11B and 11C can be of any shape that is able to be held on the outer surface of the adjacent legs 8a, 8b and 8c avoiding dropping off.

Meanwhile, in the first, second and third tubular-body forming elements 4A, 4B and 4C forming the single tubular body 2, the bend parts 7a, 7b and 7c are arranged in multistage along the axial direction of the tubular body 2 formed with the tubular-body forming elements 4A, 4B and 4C by providing some of the linear legs 8a, 8b and 8c with the longer linear sections, the joint sections 9, concatenating the vertically adjacent tubular-body forming sections 5. Consequently, when the first, second and third tubular-body forming elements 4A, 4B and 4C are assembled and unified to form the tubular body 2, each of the tubular-body forming elements 4A, 4B and 4C is wound in a cylindrical shape to form the outer surface of the tubular body 2, as shown in FIGS. 1 and 2, to facilitate deformation of the whole tubular body 2 ensuring its flexibility to deform easily in accordance with curvatures of vessels.

The connecting members 11A, 11B and 11C connecting the first, second and third tubular-body forming elements 4A, 4B and 4C thus wound and assembled in a cylindrical shape to form the outer surface of the tubular body 2 are spirally arranged on the outer surface of the tubular body 2 as shown in FIGS. 1 and 2, facilitating twist deformation of the tubular body 2.

As described above, since the vascular stent 1 according to the embodiment is easily bent along the longitudinal direction without generating heavy load and is twisted as well, when the blood vessel in which this vascular stent 1 has been implanted become bent or twisted, the vascular stent 1 can deform in accordance with the bend or twist of the blood vessel, thus suppressing hyperplasia and decreasing the possibility of restenosis therein.

In addition, in the tubular body 2 in accordance with the embodiment, by assembling the tubular-body forming elements 4 without overlapped portion thereof, the smooth outer surface and inner surface of the tubular body 2 in which a flow channel is formed is obtained. In the vascular stent 1 formed by using a tubular body 2 like this, since the inner and outer surfaces are smooth, when it is implanted in a vessel in a living body, it provides uniform scaffolding for the inner wall of a blood vessel along the entire length of the vascular stent 1 and ensures smooth flow of blood within this vascular stent 1.

Although the embodiment described above shows the vascular stent 1 formed by assembling three tubular-body forming elements 4A, 4B and 4C, two or four tubular-body forming elements can be assembled to form a vascular stent 1.

Moreover, though two adjacent connecting members each attaching to each of the adjacent legs are melt-welded to connect in the above description, it is also possible to attach more than one connecting members to each adjacent leg to be melt-welded to connect and unify the tubular body-forming element 4A, 4B and 4C.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A vascular stent to be implanted in a vessel of a living body to scaffold the vessel from inside, the vascular stent comprising;
   a plurality of tubular-body forming elements constituting a part of a tubular body, wherein the tubular body includes three tubular-body forming elements, said tubular-body forming elements being formed by bending a strand made of a first biodegradable polymer such that a linear part and a bend part alternate in sequence;
   at least two connecting members made of a second biodegradable polymer, each of the at least two connecting members formed around a respective one of the tubular-body forming elements,
   wherein said tubular-body forming elements are combined together to form said tubular body providing a single flow channel therein from a first end to a second end, and
   wherein said tubular-body forming elements combined together are unified to form said single tubular body by melt-welding the at least two connecting members, wherein each of the at least two connecting members is attached to a different one of the tubular-body forming elements, and wherein the at least two connecting members are adjacent to each other.

2. The vascular stent according to claim 1, wherein said tubular-body forming elements are formed such that the bend parts are arranged in multistage along the axial direction of said tubular body by providing a longer linear portion in some of the linear parts.

3. The vascular stent according to claim 1, wherein said tubular-body forming elements are wound in a cylindrical shape to form a circumferential side of said tubular body.

4. The vascular stent according to claim 1, wherein the second biodegradable polymer is substantially a same type as the first biodegradable polymer.

5. The vascular stent according to claim 1, wherein said connecting member is formed of a biodegradable polymer having a melting point lower than a melting point of the biodegradable polymer forming said strand.

6. The vascular stent according to claim 1, wherein the first biodegradable polymer is a polylactic acid, and said strand and said connecting member are formed of a substantially same type of polylactic acid.

7. The vascular stent according to claim 1, wherein said plurality of tubular-body forming elements are combined without having an overlapping portion to form said tubular body.

8. The vascular stent according to claim 1, wherein said strand forming said tubular-body forming element is a non-interrupted continuous monofilament.

9. The vascular stent according to claim 1, wherein each of the tubular-body forming elements are formed by bending the strand to produce two peaks and two valleys for each of a plurality of stages.

10. The vascular stent according to claim 2, wherein a starting point of bending for a second stage is displaced from a starting point of bending for a previous stage by approximately 120 degrees on a circumference of the tubular body.

11. The vascular stent according to claim 2, wherein each of the at least two connecting members is formed as a cylinder through which a tubular-body forming element is inserted.

12. A vascular stent to be implanted in a vessel of a living body to scaffold the vessel from inside, the vascular stent comprising;
   a plurality of tubular-body forming elements constituting a part of a tubular body, said tubular-body forming elements being formed by bending a strand made of a first biodegradable polymer such that a linear part and a bend part alternate in sequence,
   at least two connecting members made of a second biodegradable polymer, each of the at least two connecting members formed around a respective one of the tubular-body forming elements, wherein the at least two connecting members are spirally arranged on a circumferential side of said tubular body,
   wherein said tubular-body forming elements are combined together to form said tubular body providing a single flow channel therein from a first end to a second end, and
   wherein said tubular-body forming elements combined together are unified to form said single tubular body by melt-welding the at least two connecting members, wherein each of the at least two connecting members is attached to a different one of the tubular-body forming elements, and wherein the at least two connecting members are adjacent to each other.

13. The vascular stent according to claim 12, wherein said tubular-body forming elements are formed such that the bend parts are arranged in multistage along the axial direction of said tubular body by providing a longer linear portion in some of the linear parts.

14. The vascular stent according to claim 12, wherein said tubular-body forming elements are wound in a cylindrical shape to form a circumferential side of said tubular body.

15. The vascular stent according to claim 12, wherein the second biodegradable polymer is substantially a same type as the first biodegradable polymer.

16. The vascular stent according to claim 12, wherein said connecting member is formed of a biodegradable polymer having a melting point lower than a melting point of the biodegradable polymer forming said strand.

17. The vascular stent according to claim 12, wherein the first biodegradable polymer is a polylactic acid, and said strand and said connecting member are formed of a substantially same type of polylactic acid.

18. The vascular stent according to claim 12, wherein said plurality of tubular-body forming elements are combined without having an overlapping portion to form said tubular body.

19. The vascular stent according to claim 12, wherein said strand forming said tubular-body forming element is a non-interrupted continuous monofilament.

20. The vascular stent according to claim 12, wherein the tubular body includes three tubular-body forming elements.

21. The vascular stent according to claim 12, wherein each of the tubular-body forming elements are formed by bending the strand to produce two peaks and two valleys for each of a plurality of stages.

22. The vascular stent according to claim 13, wherein a starting point of bending for a second stage is displaced from a starting point of bending for a previous stage by approximately 120 degrees on a circumference of the tubular body.

23. The vascular stent according to claim 13, wherein each of the at least two connecting members is formed as a cylinder through which a tubular-body forming element is inserted.

* * * * *